United States Patent [19]

Handa et al.

[11] 4,059,610

[45] Nov. 22, 1977

[54] PROCESS FOR PREPARING ISOCYANIC ACID DERIVATIVES

[75] Inventors: Susumu Handa, Wakayama; Yoshiaki Tanaka, Osaka; Atsushi Nishibata, Wakayama; Sadashi Ueda, Wakayama; Yoshiaki Inamoto, Wakayama; Masahiro Saito, Wakayama; Fumio Tanimoto, Kyoto; Hisao Kitano, Osaka, all of Japan

[73] Assignee: Kao Soap Co., Ltd., Tokyo, Japan

[21] Appl. No.: 686,381

[22] Filed: May 14, 1976

[30] Foreign Application Priority Data

May 21, 1975 Japan .................... 50-60601

[51] Int. Cl.$^2$ ............................ C07C 118/00
[52] U.S. Cl. ................... 544/193; 260/47 R; 260/77.5 NC; 560/229; 560/88; 560/196; 260/296 C; 260/347.7; 260/453 P; 260/463; 260/465.4; 260/465 D; 560/226; 560/227; 544/222; 526/291; 526/293; 526/294

[58] Field of Search ......... 260/453 P, 248 NS, 475 R, 260/482 R, 485 J, 296 C, 347.7, 47 R, 81, 82, 88.1 R

[56] References Cited

U.S. PATENT DOCUMENTS 3,440,270 4/1969 McMaster et al. ............ 260/453 P
3,920,644 11/1975 Randa et al. ................. 260/248 NS

*Primary Examiner*—Dolph H. Torrence
*Attorney, Agent, or Firm*—Blanchard, Flynn, Thiel, Boutell & Tanis

[57] ABSTRACT

Isocyanic acid derivatives are prepared by reacting an organic halogen compound with an alkali cyanate in N,N-disubstituted organic acid amides, N,N-disubstituted sulfonic acid amides, sulfoxides, sulfones or macrocyclic polyethers, at 70° to 200° C, in the presence of organic polyhalogen compounds selected from compounds having dihalogenomethyl group, dihalogenomethylene group, or trihalogenomethyl group and tetrahalogenomethane, in an amount in the range of from 1 to 20 weight percent based on the weight of said organic halogen compounds.

10 Claims, No Drawings

PROCESS FOR PREPARING ISOCYANIC ACID DERIVATIVES

BACKGROUND OF THE INVENTION

FIELD OF THE INVENTION

This invention relates to an improved process for preparing isocyanic acid derivatives.

It is a primary object of this invention to provide a process in which the isocyanic acid derivatives having a isocyanatomethyl group and/or isocyanurate ring structure can be readily and economically prepared.

Said isocyanic acid derivatives are very valuable as starting materials for polymer materials such as polyurethanes, polyureas, polyisocyanurates and so on, in the fields of the synthetic resin and coating industries and other industrial fields.

SUMMARY OF INVENTION

We made various research works for many years on preparations and applications of isocyanic acid derivatives, and we have now completed an important process.

More specifically, it has now been found that in reacting an organic halogen compound containing a halogenomethyl or halogenomethylene group with an alkali cyanate at 70° to 200° C in at least one organic compound selected from the group consisting of N,N-disubstituted organic acid amides, N,N-disubstituted sulfonic acid amides, dialkylsulfoxides, dialkylsulfones, polymethylene sulfoxides, polymethylene sulfoxides and macrocyclic polyethers, if at least one organic polyhalogen compound selected from the group consisting of compounds containing a dihalogenomethyl group, compounds containing a dihalogenomethylene group, compounds containing a trihalogenomethyl group and tetrahalogenomethanes is made present in an amount of 1 to 20% by weight based on said organic halogen compound, isocyanic acid derivatives can be obtained very conveniently and advantageously.

By "at least one organic compound selected from the group consisting of N,N-disubstituted organic acid amides, N,N-disubstituted organic sulfonic acid amides, dialkylsulfoxides, dialkylsulfones, polyalkylene sulfoxides, polyalkylene sulfones and macrocyclic polyethers" there is meant one of the compounds specifically mentioned below, a mixture of two or more of these compounds and a mixture comprising as the main component one or more of these compounds (an organic solvent free of an active hydrogen atom is used as the auxiliary component).

Specific examples of the compounds of the above-mentioned group are dimethylformamide, diethylformamide, methylethylformamide, dipropylformamide, dibutylformamide, N,N-dimethylacetamide, N-methyl-N-ethylacetamide, N,N-dipropylacetamide, N,N-dibutylacetamide, N-methylpyrolidone, N-ethylpyrrolidone, N-methyldiacetamide, tetramethylurea, N-formylmorpholin, N-acetylmorpholine, N-formylpiperidine, N-acetylpiperidine, N,N'-diformylpipeazine, N,N'-diacetylpiperazine, N-methylmaleimide, N-methylsuccinimide, N,N-dimethylbenzamide, N-methylphthalimide, N,N-dimethylbenzene sulfonamide, N,N-dimethyltoluene sulfonamide, dimethylsulfoxide, diethylsulfoxide, dimethylsulfone, diethylsulfone, tetramethylene sulfoxide, tetramethylenesulfone, pentamethylene sulfoxide, pentamethylene sulfone, methyltetramethylene sulfoxide, methyltetramethylene sulfone, 9-curaune-3, 12-curaune-4, 15-curaune-5, 18-curaune-6, benzo-15-curauene-5, dibenzo-18-curaune-6, cyclohexyl-12-curaune-4, tetramethyl-12-curaune-4, dicyclohexyl-14-curaune-4, cyclohexyl-15-curaune-5, dicyclohexyl-18-curanune-6 and the like. Among them are industrially advantageous dimethylformamide, diethylformamide, N,N-dimethylacetamide, N-methylpyrrolidone, tetramethylurea, N-formylmorpholine, N-acetylmorpholine, N-formylpiperidine, N-acetylpiperidine, N,N-dimethylbenzene sulfonamide, N,N-dimethyltoluene sulfonamide, dimethylsulfoxide, dimethylsulfone, tetramethylene sulfoxide, tetramethylene sulfone, 15-curaune-5 and 18-curaune-6.

By "an organic compound containing a halogenomethyl or halogenomethylene group" there is meant one of the compounds mentioned below, a mixture of two or more of these compounds and a mixture containing as the main component one or more of these compounds.

Specific exampls of compounds of this group are halogenoalkanes, dihalogenoalkanes, halogenoalkenes, dihalogenoalkenes, halogenoethers, dihalogenoethers, halogenoacetals, dihalogenoacetals, halogenoketals, dihalogenoketals, halogenoesters, dihalogenoesters, halogenothioethers, dihalogenothioethers, halogenonitriles, dihalogenonitriles, halogenoaralkanes, halogenohaloaralkanes, dihalogenoaralkanes, dihalogenohaloaralkanes, halogenoaralkyl ethers, dihalogenoaralkyl ethers, halogenoaralkyl ketones, halogenohaloaralkyl ethers, dihalogenoaralkyl ketones, dihalogenohaloaralkyl ethers, and derivatives of these compounds having on a halogen-free methyl, methylene, methine or aromatic hydrocarbon group at least one substituent selected from alkyl, alkoxy, acyl, alkylthio, phenyl, naphthyl, cyano, cyanate, isocyanato, cyanurato, isocyanurato, carbamyl, carbamino, perfluroalkyl and urethidino groups.

Among these compounds, a great number of compounds are industrially important, and typical instances of these important compounds are mentioned below by reference to organic chlorine compounds alone. Prefixes such as normal, secondary, iso, tertiary, ortho, meta and para are omitted to avoid complexity.

Examples of such important organic compounds include $C_{1-18}$ alkyl chlorides such as methyl chloride, ethyl chloride, propyl chloride, butyl chloride, amyl chloride, hexyl chloride, heptyl chloride, octyl chloride, nonyl chloride, decyl chloride, dodecyl chloride, tetradecyl chloride, hexadecyl chloride, and octadecyl chloride; chlorinated paraffin, cyclohexyl chloride, cyclopentyl chloride, dichloroethane, dichloropropane, dichlorobutane, dichloropentane, dichlorohexane, allyl chloride, crotyl chloride, butenyl chloride, propargyl chloride, 1,4-dichlorobutene-2, di(chloromethyl)ether, di(chloroethyl)ether, di(chloropropyl)ether, di(chlorobutyl)ether, chlorodimethyl ether, chlorodiethyl ether, chlorodipropyl ether, methylchloroethyl ether, propylchloroethyl ether, butylchloroethyl ether, triethylene glycol dichloride, tetraethylene glycol dichloride, polyethylene glycol dichloride, di(chloroethyl)formal, di(chloroethyl)acetal, di(chloroethyl)butyral, ethylchloroethylacetal, di(chloroethyl)acetone ketal, chloroacetone, dichloroacetone, chlorocyclohexanone, dichlorocyclohexanone, chloroacetone methylketal, dichloroacetone dimethylketal, chloroacetic acid esters, chloroethyl chloroacetate, di(chloroethyl)maleate, di(chloroethyl) succinate, di(chloroethyl) adipate, di(- chloroethyl) phthalate, di(chloroethyl) carbonate, chlorodimethyl thioether, chlorodiethyl thioether, di(chloromethyl) thioether, di(chloroethyl) thioether, chloroacetonitrile, chloropropionitrile, chlorobutyronitrile, chlorocapronitrile, dichloroadiponitrile, benzyl chloride, chlorobenzyl chloride, methylbenzyl chloride, methoxybenzyl chloride, nitrobenzyl chloride, cyanobenzyl chloride, isocyanatomethylbenzyl chloride, xylylene dichloride, chloroxylylene dichloride, methylxylylene dichloride, dimethylxylydine dichloride, methoxyxylylene dichloride, isocyanatomethylxylylene dichloride, trichloropseudocumene, trichloromesitylene, tetrachlorodurene, chloromethylbiphenyl, chloromethylnaphthalene, chloromethylcyclopentadiene, chloromethylfuran, chloromethylpyridine, chloromethyldiphenyl ether, di(chloromethylphenyl) ether, di(chloromthylphenyl) thioether, di(chloromethylphenyl)sulfone, di(chloromethylphenyl) sulfoxide, dichloromethylbenzidine, phenacyl chloride, chloromethylphenylmethyl ketone, chloromethylphenacyl chloride, chloromethylbenzophenone, di(chloromethyl)benzophenone, chloromethylnaphthylalkyl ethers, di(chloromethylnaphthyl) ether, chloromethylbisphenol A, bis(chlorocyclohexyl), bis(chlorocyclohexyl) ether, bis(chloromethyl)dichlorohexyl, chlorinated petroleum hydrocarbons, chlorinated alkylbenzenes, chloromethylated coal tar hydrocarbons, chloromethylated terpene hydrocarbons, chloromethylated polystyrenes, chloromethylated petroleum resins, chloromethylated coumaroneindene resins, chloromethylated polyterpenes, chloromethylated phenols and chloromethylated phenolic resins.

As the alkali cyanate, there is employed at least one member selected from the group consisting of lithium cyanate, sodium cyanate, potassium cyanate, rubidium cyanate, cesium cyanate and ammonium cyanate. Sodium cyanate or potassium cyanate having a purity of at least 70% is industrially important.

By "at least one organic polyhalogen compound selected from the group consisting of compounds containing a dihalogenomethyl group, compounds containing a dihalogenomethylene group, and compounds containing a trihalogenomethyl group and tetrahalogenomethanes" there is meant the compounds mentioned below. Industrially important compounds include organic polyfluorine compounds, organic polychlorine compounds, organic polybromine compounds and organic polyiodine compounds, typical instances of which are mentioned below. Prefixes such as normal, secondary, iso, tertiary, ortho, meta and para are omitted in order to avoid complexity.

More specifically, industrially important compounds include dichloromethane, dibromomethane, di iodomethane, chloroform, bromoform, iodoform, carbon tetrachloride, carbon tetrabromide, carbon tetraiodide, dichlorodifluoromethane, fluorotrichloromethane, trifluoromethane, trifluorobromomethane, trifluoroiodomethane, trichloroethylene, tetrachloroethylene, perchlorobutadiene, trichloroethane, tetrachloroethane, pentachloroethane, hexachloroethane, tribromoethane, tetrabromoethane, trichloroethylene dibromide, tetrachloroethylene dibromide, tetrafluoroethylene dichloride, trifluorotrichloroethane, tetrafluoroethylene dibromide, trifluorochlorodibromoethane, hexafluoropropene dichloride, hexafluoropropene dibromide, fureons, perfluorobutadiene tetrachloride, perfluorobutadiene tetrabromide, chloral, chloral acetal, pentachloroacetone, pentachloroacetone ketal, hexachloroacetone, pentachloroacetone, pentachloroacetone ketal, hexachloroacetone, hexachloroacetone ketal, pentaluoroacetone, pentafluoroacetone ketal, hexafluoroacetone, hexafluoroacetone ketal, trichlorotrifluoroacetone, tetrachlorodifluoroacetone, pentachlorofluoroacetone, dichlorotetrafluoracetone, chloropentafluoroacetone, trichloroacetonitrile, trifluoroacetonitrile, tribromoacetonitrile, dichloroacetonitrile, dichlorofluoroacetonitrile, chlorodifluoroacetonitrile, trifluoroacetic acid esters, perfluorofatty acid esters, perfluoroalkanes, perfluoroalkenes, perfluoroalkyl ethers, perfluoroalkylbenzenes, perfluorofatty acid amides, benzal chloride, chlorobenzal chloride, benzotrichloride, chlorobenzotrichloride, benzal fluoride, chlorobenzal fluoride, benzotrifluoride, chlorobenzotrifluoride, trifluoromethylbenzal fluoride, trifluoromethylbenzotrifluoride, chlorodifluoromethylbenzene, dichlorofluoromethylbenzene, bromodifluoromethylbenzene, dibromofluoromethylbenzene, chlorodifluoromethylbenzotrifluoride, dichlorofluoromethylbenzotrichloride, dichlorofluoromethylbenzotrifluoride, perfluoroalkyl thioethers, perfluoroalkyl amines, perfluoroalkyl phosphoric acid esters, perfluoroalkyl chlorides, perfluoroalkyl bromides, perfluoroalkyl iodides, and the like. Macromolecular compounds having no affinity or compatibility with organic compounds or organic halogen compounds as reaction solvents are excluded from the organic polyhalogen compounds. As a result of experiments it was confirmed that fluorinated lubricating oils, fluorinated greases and fluorine resins have no substantial effects in the process of the present invention.

The "isocyanic acid derivative" referred to in the present invention includes isocyanic acid esters (isocyanates), diisocyanic acid esters (diisocyanates), polyisocyanic acids (polyisocyanates) and corresponding compounds containing an isocyanuric ring. More specifically, there are included isocyanic acid esters, isocyanic acid esters and isocyanuric acid esters, diisocyanic acid esters, diisocyanic acid esters and polymers thereof, polyisocyanic acid esters, polyisocyanic acid esters and polymers thereof, isocyanic acid-isocyanuric acid esters, diisocyanic acid-isocyanuric acid esters, diisocyanic acid-polyisocyanuric acid esters, polyisocyanic acid-isocyanuric acid esters and polyisocyanic acid-polyisocyanuric acid esters. These compounds may be obtained singly or in the form of mixtures of two or more of them. Further, oligomers and polymers of isocyanic acid esters comprising as the main component one or more of the foregoing compounds are included.

More specifically, isocyanic acid esters, isocyanuric acid esters which are trimers of isocyanic acid esters, and composites of these which include both low-molecular-weight and high-molecular-weight compounds are included in the isocyanic acid derivative in the present invention. In short, all of these compounds are included in the intended product of the present invention. Whether the obtained product has a low molecular weight or a high molecular weight is decided depending on the kind of the starting organic halogen compound, namely the number of reactive halogen atoms in the molecule, and on reaction conditions.

If an organic halogen compound containing one reactive halogen atom is expressed as R-X and an alkali cyanate is expressed as MNCO, the reaction between them is expressed as follows:

R-X + MNCO → R-NCO + MX and an isocyanic acid ester R-NCO and an alkali halide MX are first obtained. The so obtained R-NCO is converted to an isocyanuric acid ester (R-NCO)₃ under the same reaction conditions in some cases as shown below:

3. (R-NCO) → (R-NCO)₃

This formula indicates that the same R-NCO is trimerized, but different isocyanic acid esters may be combined or isocyanic acid HNCO or its salt may be included into such trimer as a part thereof.

If an organic halogen compound containing two reactive halogen atoms is expressed as X-R-X, the reaction is expressed as follows:

X-R-X + MNCO → X-R-NCO + MX

X-R-NCO + MNCO → OCN-R-NCO + MX

Namely, a halogen-containing isocyanate X-R-NCO is first formed and a diisocyanic acid ester OCN-R-NCO is then formed. If suitable reaction conditions are chosen, the reaction advances in one stage as follows:

X-R-X + 2MNCO → OCN-R-NCO + 2MX

Under conditions causing trimerization, the thus formed X-R-NCO or OCN-R-NCO is converted to an isocyanuric acid ester as shown below, and if this ester contains X in the terminal group, it is further substituted with excessive MNCO and a triisocyanate-triisocyanurate is finally formed. Of course, in this case, diisocyanic acid esters to be trimerized need not have the same structure, and trimers containing a diisocyanato-isocyanuric acid salt or a diisocyanato-isocyanuric alkyl ester are formed under some conditions.

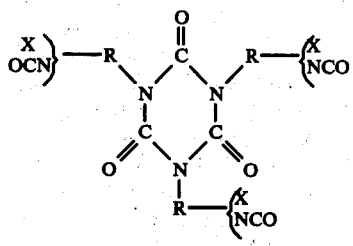

When trimerization is repeated in the terminal group of the above-mentioned isocyanato group-terminated isocyanuric acid ester, the low-molecular-weight ester is polycondensed in succession to a high-molecular-weight compound, and finally, a polyisocyanurate type resin is formed. This feature, however, is not the main aspect of the present invention. When organic halogen compounds containing at least 3 reactive halogen atoms, such as tris(2-chloroethyl) ether of trimethylol propane, tetrakis(2-chloroethyl) ether of pentaerythritol, tri(chloromethyl)benzene, tetra(chloromethyl)benzene, tri(2-chloroethyl) cyanurate, tri(2-chloroethyl) isocyanurate and tri(2-chloroethoxyethyl) isocyanurate, are used as the starting compounds, if a sufficient amount of an alkali cyanate is used, formation of high-molecular-weight products takes place at a higher probability than in the case where X-R-X is used as the starting compound. Accordingly, studies have been required for obtaining valuable isocyanic acid derivatives. As is apparent from the foregoing illustration, the intended product of the process of the present invention includes not only isocyanic acid esters but also isocyanuric acid esters, and from the industrial viewpoint, it is important to obtain as the reaction product a compound having an isocyanato group at the terminal end of the substituent.

Both isocyanato group-containing compounds and isocyanuric ring-containing compounds are inclusively mentioned as isocyanic acid derivatives, and it will readily be understood that both the types of compounds can be obtained in the same reaction system according to the process of the present invention.

The above-mentioned reaction of the present invention is carried out at 70° to 200° C, preferably 80° to 180° C, mainly in the liquid phase. More specifically, an organic compound such as mentioned above is used as a solvent and the alkali cyanate is reacted with an organic halogen compound as mentioned above in such a state that the alkali cyanate is dispersed in the solvent. In short, the reaction is conducted in a heterogeneous system (in a slurry state in some case). The method of addition of the organic halogen compound is not particularly critical. For example, all of the organic halogen compound may be added at the start of the reaction, or it may be added gradually as the reaction advances. Further, it may be added continuously before or after addition of other starting compounds. The process of the present invention can be performed batchwise or in a continuous manner.

The problem encountered in practicing the reaction of the present invention is that since an organic halogen compound having a high reactivity is used as the starting compound and an isocyanic acid ester having a high reactivity is treated as a primary product, various side reactions take place. Occurrence of these side reactions is enhanced when an alkali cyanate having a low purity is used or an organic compound which is not sufficiently purified is employed as the solvent or when too severe reaction conditions are adopted. In this case, the yield of the intended product is lowered and the quality of the product is degraded.

Side reactions will now be described by reference to the case where an alkyl halide is used as the organic halogen compound. Considerable amounts of a dialkyl carbonate, a dialkyl parabanate, a dialkyl urea, a trialkyl biuret, an olefin, a decomposition product of an adduct of the alkyl halide and the solvent, and a tar-like material are formed as by-product, whereby separation and purification of the product become very difficult. Especially when the reaction is conducted semi-continuously or in a continuous manner, the operation is very difficult.

Accordingly, we made various research works with a view to developing a process capable of preventing occurrence of these side reactions, and as a result, it was found that when at least one organic polyhalogen compound selected from the group consisting of compounds containing a dihalogenomethyl group, compounds containing a dihalogenomethylene group, compounds containing a trihalogenomethyl group and tetrahalogenomethanes, such as exemplified above, is made present in an amount of 1 to 20% by weight, preferably 2 to 18% by weight, based on the organic halogen compound as the main starting compound, occurrence of side reactions can be effectively prevented. What is more important is that a considerable amount of the isocyanato group is incorporated in the reaction product by the use of the organic polyhalogen compound. By this meritorious feature, the process of the present invention can be distinguished from the conventional processes for the preparation of isocyanuric acid esters.

In the practical operation, the organic polyhalogen compound is added at the start of the reaction or in the midway of the reaction. It is convenient to add the organic polyhalogen compound in advance to the starting organic halogen compound or the organic compound to be used as the solvent. The organic polyhalogen compound has an effect of leading the reaction advantageously to the intended direction, but it is not changed by the reaction and it is recovered by a suitable operation after completion of the reaction. Namely, through various experiments made by us, it has been confirmed that the organic polyhalogen compound acts as a very effective negative catalyst to side reactions.

The process of the present invention does not require a special apparatus, and it can be conducted in an ordinary chemical reaction vessel under atmospheric or elevated pressure. Separation of the intended product from the reaction mixture can be performed by distillation, filtration, crystallization, precipitation, centrifugal separation, extraction or suitable combinations of these separation methods. The manner of the combination or the order of the combined operations is appropriately decided based on properties of the reaction mixture and the reaction product.

We made various experiments on the above-mentioned process of the present invention and we confirmed the advantages of the present invention based on these experiments. In order to illustrate the technical content of the present invention, typical Examples extracted from these experiments will now be described. Of course, it must be noted that the process of the present invention is not limited to the embodiments shown in these Examples.

EXAMPLE 1

A reaction flask was charged with amounts indicated in Table 1 of benzyl chloride, sodium cyanate having a purity of 100%, dimethylformamide and an organic polyhalogen compound. The mixture was heated at 80° C under agitation. At every 30 minutes, a prescribed amount of the reaction mixture was taken out and added to ice water, and the aqueous solution was analyzed to examine the effect of the organic polyhalogen compound based on the conversion. On the assumption that this reaction was a second-order reaction, the speed constant K (l/mole.sec) was calculated from the conversion to obtain results shown in Table 1.

Table 1

| Benzyl Chloride (g) | Sodium Cyanate (g) | Dimethyl-formamide (ml) | Organic Polyhalogen Compound | | k ($\times 10^{-2}$) |
|---|---|---|---|---|---|
| | | | chemical formula | amount used (g) | |
| 0.2361 | 0.1002 | 375 | $CBr_4$ | 0.1286 | 1.22 |
| 0.4805 | 0.2007 | 750 | $CBr_4$ | 0.0524 | 1.45 |
| 0.4651 | 0.2008 | 750 | $CHI_3$ | 0.3054 | 0.81 |
| 0.4776 | 0.2008 | 750 | $C_2Cl_6$ | 0.1835 | 1.22 |
| 0.4689 | 0.2004 | 750 | not added | not added | 1.21 |

In the runs of Table 1, when the organic polyhalogen compound was not used, tribenzyl isocyanurate was formed as the reaction product, and dibenzyl parabanate was formed as a by-product. When the organic polyhalogen compound was added, benzyl isocyanate was formed as the main product and tribenzyl isocyanurate was formed as the by-product. The reaction speed was not remarkably high under the above reaction conditions, but there was observed an advantage that a parabanic acid ester or the like was not formed as a by-product.

EXAMPLE 2

A reaction flask was charged with an organic polyhalogen compound indicated in Table 2, 12.7 g of benzyl chloride, 7.2 g of sodium cyanate having a purity of 90% and 73.1 g of dimethylformamide, and the mixture was agitated in a nitrogen gas current and reacted at 140° C for 20 minutes. The reaction mixture was cooled. The precipitated inorganic salts were removed from the reaction mixture by filtration. The filtrate was collected and dimethylformamide was removed therefrom at a low temperature by distillation under reduced pressure. The reaction product was analyzed to obtain results shown in Table 2. When the organic polyhalogen compound was not added in this reaction, a tar-like substance was formed as a by-product and the overall yield of benzyl isocyanate and tribenzyl isocyanurate was only about 70%.

Table 2

| Organic Polyhalogen Compound | | Yield (%) of Benzyl Isocyanate | Yield of (%) Tribenzyl Isocyanurate |
|---|---|---|---|
| chemical formula | amount used (g) | | |
| $CBr_4$ | 3.3 | 62 | 28 |
| $CBr_4$ | 1.7 | 59 | 30 |
| $(CHBr_2)_2$ | 3.5 | 51 | 37 |
| $C_2Cl_6$ | 2.4 | 20 | 75 |
| $CCl_4$ | 1.5 | 5 | 86 |
| $CHI_3$ | 3.9 | 75 | 19 |

EXAMPLE 3

A reaction flask was charged with an organic polyhalogen compound indicated in Table 3, 32 g of p-chlorobenzyl chloride, 10 g of sodium cyanate having a purity of 100% and 150 g of N,N-dimethylacetamide, and the mixture was maintained at 100° C for 60 minutes under agitation in a carbon dioxide gas current. The inorganic salts were removed from the reaction mixture by filtration, and the filtrate was collected and N,N-dimethylacetamide was removed at a low temperature by distillation under reduced pressure. The reaction product was analyzed to obtain results shown in Table 3.

Table 3

| Organic Polyhalogen Compound | | Yield (%) of p-Chlorobenzyl Isocyanate | Yield (%) of Tris(p-chloro-benzyl) Isocyanurate |
|---|---|---|---|
| chemical formula | amount used (g) | | |
| $CBr_4$ | 3.32 | 24 | 65 |
| $CF_3I$ | 2.05 | 25 | 67 |
| $CBrCl_3$ | 1.98 | 18 | 58 |
| $(CHBr_2)_2$ | 3.46 | 30 | 50 |
| $CHBr_3$ | 2.63 | 25 | 45 |
| $CH_2Br_2$ | 1.74 | 34 | 36 |
| $CF_3CF_2CF_2I$ | 3.50 | 29 | 55 |
| $C_6H_4(CF_3)_2$ | 5.02 | 30 | 51 |
| $C_4Cl_6$ | 4.05 | 27 | 56 |
| $CF_3CF_2CN$ | 5.10 | 25 | 52 |

When the above reaction was conducted without addition of the organic polyhalogen compound, only an overall yield of 30%, namely 10% of p-chlorobenzyl isocyanate and 20% of tris(p-chlorobenzyl) isocyanurate, was obtained. When tetrabromomethane was used as the organic polyhalogen compound, if 3 g of potassium bromide or tetramethyl ammonium bromide was added as the assistant, the yield of p-chlorobenzyl isocyanate was increased by 7% or 6%, and the overall yield of p-chlorobenzyl isocycanate and tris(p-chlorobenzyl) isocyanurate was elevated to 95% or higher.

EXAMPLE 4

A reaction flask was charged with 10 moles of an organic compound indicated in Table 4 as the solvent, 1 mole of p-methylbenzyl chloride, 2 moles of sodium cyanate having a purity of 95% and 0.1 mole of carbon tetrabromide, and the mixture was reacted at 120° C for 1 hour. The reaction mixture was cooled and the precipitated inorganic salts were removed. The filtrate was analyzed to determine the yield of p-methylbenzyl isocyanurate. The solvent was recovered by distillation under reduced pressure and the recovery ratio was determined. Results obtained are shown in Table 4.

Table 4

| Organic Compound as Solvent | Yield (%) of p-Methyl-benzyl Isocyanate | Yield (%) of Tri(p-methylbenzyl) Isocyanurate | Solvent Recovery Ratio (%) |
|---|---|---|---|
| dimethylformamide | 40 | 54 | 88 |
| diethylformamide | 39 | 50 | 89 |
| N,N-dimethylacetamide | 37 | 46 | 92 |
| N-methylpyrrolidone | 25 | 48 | 85 |
| N-methyldiacetamide | 17 | 38 | 79 |
| tetramethylurea | 45 | 52 | 95 |
| N-formylpiperidine | 37 | 41 | 85 |
| N-formylmorpholine | 38 | 40 | 87 |
| N-acetylmorpholine | 36 | 42 | 80 |
| N,N-dimethylbenzamide | 23 | 33 | 84 |
| N,N-dimethylbenzene sulfonamide | 17 | 25 | 81 |
| dimethylsulfoxide | 25 | 51 | 82 |
| dimethylsulfone | 25 | 15 | 80 |
| tetramethylene sulfoxide | 15 | 48 | 85 |
| tetramethylene sulfone | 20 | 10 | 95 |
| 15-curaune-5 | 42 | 49 | 92 |
| 18-curaune-6 | 45 | 45 | 94 |

In case the yield was low, for example, when N-methyldiacetamide, N,N-dimethylbenzamide, N,N-dimethylbenzene sulfonamide, dimethylsulfone, tetramethylene sulfoxide or tetramethylene sulfone was employed, the yield could be remarkably improved by prolonging the reaction.

EXAMPLE 5

A stainless steel reaction vessel equipped with a cooling jacket-provided distillation tube, an agitator, a dropping funnel and a thermometer was charged with 100 g of sodium cyanate having a purity of 95%, 500 g of dimethylformamide, 50 g of an organic polyhalogen compound indicated in Table 5 and 5 g of tetramethyl ammonium bromide, and while the mixture was being heated 140° C under agitation, 1.5 moles of a cooled starting organic halogen compound was added dropwise over a period of 30 minutes. The reaction was continued for 2 hours, during which a low-boiling-point liquid distilled from the distillation tube was collected in a trap. This liquid was a mixture of the starting organic halogen compound and the isocyanic acid ester formed. The yield of the isocyanic acid ester was determined by the re-fractionation or analysis method. The mixture in the reaction vessel was cooled, and the inorganic salts were removed by filtration and the filtrate was fractionated to separate it into dimethylformamide and the isocyanuric acid ester formed. The yield of the latter was determined. Results are shown in Table 5.

Table 5

| Starting Organic Halogen Compound (chemical formula) | Organic Polyhalogen Compound (chemical formula) | Yield (%) of Isocyanic Acid Ester | Yield (%) of Isocyanuric Acid Ester |
|---|---|---|---|
| $CH_3Cl$ | $CBr_4$ | 35 | 31 |
| $C_2H_5Cl$ | $C_2H_2Cl_2Br_2$ | 42 | 30 |
| $n\text{-}C_3H_7Cl$ | $C_2H_2Cl_2Br_2$ | 40 | 30 |
| $CH_3COCH_2Cl$ | $C_2F_3ClBr_2$ | 21 | 52 |
| $ClCH_2CN$ | $CF_2I_2$ | 25 | 48 |
| $CH_2=CHCH_2Cl$ | $CF_2I_2$ | 45 | 43 |
| $CH_3Br$ | $C_2H_2Br_4$ | 42 | 50 |
| $C_2H_5Br$ | $C_2H_3ClBr_2$ | 44 | 51 |
| $CH_3I$ | $CI_4$ | 37 | 55 |
| $C_2H_5I$ | $CI_4$ | 40 | 51 |
| $CH_2=CHCH_2Br$ | $C_2H_2Cl_2Br_2$ | 46 | 50 |
| $CH_3OCH_2CH_2Cl$ | $CBr_4$ | 36 | 23 |
| $CH_2SCH_2CH_2Cl$ | $CBr_4$ | 38 | 34 |
| $ClCH_2COOCH_3$ | $CBr_4$ | 10 | 39 |

In runs of Table 5 where $CH_3COCH_2Cl$, $ClCH_2CN$ or $ClCH_2COOCH_3$ was used as the starting compound, the yield of the isocyanuric acid ester was the total yield of the isocyanuric acid ester and the cyanuric acid ester.

EXAMPLE 6

A flask equipped with an agitator, a reflux cooler and a thermometer was charged with 1 mole of a starting organic halogen compound indicated in Table 6, 100 g of lithium cyanate having a purity of 95%, 40 g of carbon tetrabromide and 400 g of diethylacetamide, and the reaction was conducted at 150° C for 1 hour and the reaction mixture was subjected to distillation under reduced pressure. The liquid was thus recovered until the residue in the flask became semisolid. The so recovered liquid was fractionated to determine the yield of the isocyanic acid ester. Results are shown in Table 6. Further, the residue in the flask was cooled and thrown in water, and the water-insoluble solid was collected and extracted with benzene. The yield of the isocyanuric acid ester was determined by distillation of the extract. Results are shown in Table 6.

Table 6

| Starting Organic Halogen Compound (chemical formula) | Yield (%) of Isocyanic Acid Ester | Yield (%) of Isocyanuric Acid Ester |
|---|---|---|
| $n\text{-}C_8H_{17}Br$ | 28 | 53 |
| $C_4H_9CH_2CH_2Cl$ | 30 | 51 |
| $C_6H_5CH_2Cl$ | 35 | 52 |
| $C_6H_5CH_2Br$ | 38 | 50 |
| $p\text{-}CH_3OC_6H_4CH_2Cl$ | 38 | 54 |
| $p\text{-}CH_3COC_6H_4CH_2Cl$ | 41 | 50 |
| $p\text{-}NO_2C_6H_4CH_2Br$ | 44 | 50 |

EXAMPLE 7

A flask equipped with an agitator, a reflux cooler and a thermometer was charged with 100 g of a starting organic halogen compound indicated in Table 7, 60 g of sodium cyanate having a purity of 90%, 30 g of carbon tetrabromide, 30 g of hexachlorobutadiene and 500 g of dimethylformamide, and the reaction was conducted at 140° – 150° C for 20 minutes. The reaction mixture was cooled and the inorganic salts were removed by filtration. The filtrate was subjected to fractionation under reduced pressure to determine the yield of the isocyanic acid ester. The residue was thrown into water and the precipitated crystals were collected. The crystals were recrystallized from ethanol and the yield of the isocyanuric acid ester was determined. Results are shown in Table 7.

Table 7

| Starting Organic Halogen Compound (chemical formula) | Yield (%) of Isocyanic Acid Ester | Yield (%) of Isocyanuric Acid Ester |
|---|---|---|
| $C_6H_5CH_2Cl$ | 37 | 48 |
| $O\text{-}ClC_6H_4CH_2Cl$ | 40 | 42 |
| $m\text{-}CH_3C_6H_4CH_2Cl$ | 36 | 37 |
| $C_{10}H_7CH_2Cl$ | 42 | 45 |
| $4\text{-}ClC_{10}H_6CH_2Cl$ | 41 | 44 |
| $C_6H_5C_6H_4CH_2Cl$ | 44 | 42 |
| $C_6H_5OC_6H_4CH_2Cl$ | 43 | 47 |
| $C_6H_5OC_6H_4CH_2Br$ | 40 | 49 |

EXAMPLE 8

A flask equipped with an agitator, a reflux cooler and a thermometer was charged with 17.5 g of p-xylene dichloride, 15 g of sodium cyanate having a purity of 95% and 100 g of dimethylformamide, and the mixture was reacted by heating it at 140° C. In 20 minutes, gelatin was caused to occur. When 1.2 to 6.0 g of potassium bromide was added to this reaction system under the same reaction conditions, gelation was caused to occur in 13 minutes. If gelation is caused to occur in the reaction mixture, post treatments such as pulverization of the gel and removal of the inorganic salts and dimethylformamide become troublesome. In the practical operation, it is convenient to perform the reaction so that gelation is not caused to occur. For this purpose, it was found, addition of an organic polyhalogen compound is very effective. More specifically, 1.5 g of tetrabromomethane was added instead of potassium bromide and the reaction was conducted for 20 minutes. The reaction mixture was filtered to remove the inorganic salts. Dimethylformamide was recovered from the filtrate, and the product was analyzed. It was found that the conversion was 93% and that the yield of the product having a terminal isocyanato group was 44% and the yield of the product having an isocyanurato group was 49%.

When this reaction was conducted by adding 2.0 g of tetrachloromethane, the conversion of substantially 100% was obtained if the reaction was continued for 30 minutes. The yield of the product having a terminal isocyanato group was about 42% and the yield of the product having an isocyanurato group was about 58%.

EXAMPLE 9

The reaction was conducted for 20 minutes under the same conditions as in Example 8 except that 0.1 mole of an organic halogen compound indicated in Table 8 was added instead of p-xylylene dichloride and 1.5 g of tetrabromomethane was added. Post treatments were conducted in the same manner as described in Example 8. Obtained results are shown in Table 8.

Table 8

| Starting Organic Halogen Compound | Conversion (%) | Yield (%) of Product Having Terminal Isocyanato Group |
|---|---|---|
| 1,4-dichlorobutene-2 | 95 | 37 |
| 1,4-dichlorobutine-2 | 90 | 45 |
| 1,4-dichlorobutane | 87 | 50 |
| 1,5-dichloropentane | 85 | 52 |
| 1,6-dichlorohexane | 86 | 62 |
| o-xylylene dichloride | 90 | 45 |
| m-xylylene dichloride | 92 | 43 |
| di(2-chloroethyl) ether | 75 | 47 |
| di(2-chloroethyl) thioether | 90 | 60 |
| di(2-chloroethoxyethyl) ether | 70 | 55 |
| 1,5-di(chloromethyl)naphthalene | 91 | 46 |
| 4,4'-di(chloromethyl)biphenyl | 93 | 44 |
| 4,4'-di(chloromethyl) diphenyl ether | 90 | 41 |
| 2,4-di(chloromethyl)anisole | 85 | 42 |

EXAMPLE 10

A reaction vessel equipped with an agitator, reflux cooler and a thermometer was charged with 35 g of p-xylylene dichloride, 30 g of sodium cyanate having a purity of 90%, 10 g of sodium bromide, 5 g of an organic polyhalogen compound indicated in Table 9 and 60 g of dimethylformamide, and the mixture was reacted at 120° C for 40 minutes. The reaction mixture was cooled and the inorganic salts was removed by filtration. The filtrate was concentrated under reduced pressure to obtain a yellowish-brown viscous liquid. The liquid was analyzed to determine the yields of the product having a terminal isocyanator group and the product having an isocyanurato group. Results are shown in Table 9.

Table 9

| Organic Polyhalogen Compound (chemical formula) | Yield (%) of Product Having Terminal Isocyanato Group | Yield (%) of Product Having Isocyanurato Group |
|---|---|---|
| $CHBr_3$ | 48 | 37 |
| $CBr_4$ | 53 | 42 |
| $C_2H_2Br_4$ | 49 | 42 |
| $p\text{-}CF_3C_6H_4Br$ | 40 | 50 |
| $3,5\text{-}(CF_3)_2C_6H_3Br$ | 35 | 52 |

EXAMPLE 11

A reaction vessel equipped with an agitator, a reflux cooler and a thermometer was charged with 0.2 mole of a starting organic halogen compound indicated in Table 10, 20 g of sodium cyanate having a purity of 100%, 3 g of tetrabromomethane and 55 g of an organic compound shown in Table 10 as the solvent. The mixture was reacted at 120° – 130° C for 1 hour, and the reaction mixture was cooled and the organic compound was removed by distillation under reduced pressure. The reaction product was extracted with benzene and benzene was removed from the extract. The yield and property of the product were examined to obtain results shown in Table 10.

Table 10

| Starting Organic Halogen Compound | Organic Compound (chemical formula) | Yield (%) | Isocyanato Group Content (%) in Product |
|---|---|---|---|
| 1,4-dichlorobutane | $CH_3SOCH_3$ | 92 | 25.8 |
| 2,4-di(chloromethyl-chlorobenzene | $CH_3CON(CH_3)_2$ | 90 | 16.5 |
| 2,5-di(chloromethyl)-chlorobenzene | $[(CH_3)_2N]_2CO$ | 93 | 16.0 |
| 1,4-dichloro-2,5-di-(chloromethyl)- | $HCON(CH_3)_2$ | 93 | 8.3 |

Table 10-continued

| Starting Organic Halogen Compound | Organic Compound (chemical formula) | Yield (%) | Isocyanato Group Content (%) in Product |
|---|---|---|---|
| chlorobenzene 2,5-di(chloromethyl)-strene | HCON(CH₃)₂ | 88 | 10.2 |
| 2,5-di(chloromethyl)- | CH₃CON(CH₂CH₂)₂O | 89 | 10.5 |

EXAMPLE 12

A reaction vessel equipped with an agitator, a reflux cooler and a thermometer was charged with 40 g of 1,2,4-tris(chloromethyl)benzene, 45 g of sodium cyanate having a purity of 95%, 10 g of hexachlorobutadiene and 100 g of dimethylacetamide, and the reaction was conducted at 140° C for 1 hour. The reaction mixture was gelled. Just before occurrence of this gelation, the reaction mixture was cooled and thrown into methylethylketone. In this case, the inorganic salts were precipitated and separated from the gelled product. The gelled product alone was thus collected, washed with methylethylketone sufficiently and dried to obtain a solid yellowish white powder of 1,2,4-tris-(isocyanatomethyl)benzene in which an isocyanuric ring was partially formed. When this product was analyzed, it was found that the isocyanato group content was 17.2%. This product was reacted with water, an alcohol, a glycol, an amine or the like to form a substance having a urea or urethane linkage.

What we claim is:

1. A process for preparing isocyanic acid derivative having a isocyanatomethyl group and/or isocyanurate ring structure, which consists essentially of reacting at 70° to 200° C (A) an organic halogen compound having a monohalogenomethyl group or monohalogenomethylene group, or mixtures thereof, with (B) an alkali cyanate selected from the group consisting of lithium cyanate, sodium cyanate, potassium cyanate, rubidium cyanate, cesium cyanate, ammonium cyanate and mixtures thereof, in (C) an organic solvent selected from the group consisting of N,N-disubstituted organic acid amines, N,N'-disubstituted organic sulfonic acid amides, dialkyl sulfoxides, dialkyl sulfones, polyalkylene sulfoxide, polyalkylene sulfone, macrocyclic polyethers and mixtures thereof, in the presence of (D) at least one polyhalogen compound selected from the group consisting of compounds having dihalogenomethyl group, dihalogenomethylene group or trihalogenomethyl group and tetrahalogenomethanes in an amount in the range of from 1 to 20 weight percent, based on the weight of said organic halogen compound (A), until isocyanic acid derivative of (A) is formed, said polyhalogen compound (D) being compatible with organic compounds or organic halogen compounds as reaction solvent and being present at the start or midway of the reaction and being effective to prevent side reactions and being unchanged by the reaction, and recovering from the reaction mixture said isocyanic acid derivative.

2. A process according to claim 1, in which said polyhalogen compound (D) is selected from the group consisting of carbon tetrachloride, carbon tetrabromide, hexachloroethane, hexachlorobutadiene, bromoform, iodoform and tetrabromoethane.

3. A process according to claim 1, in which the amount of said polyhalogen compound (D) is from 2 to 18 weight percent based on the weight of organic halogen compound (A).

4. A process according to claim 1, in which said organic solvent (C) is selected from the group consisting of dimethylformamide, diethylformamide, N,N-dimethylacetamide, N,N-diethylacetamide, N-methylpyrrolidone, dimethylsulfoxide and their mixtures.

5. A process according to claim 1, in which said organic halogen compound (A) is selected from the group consisting of alkyl chlorides, alkenyl chlorides, aralkyl chlorides and their bromides.

6. A process according to claim 5, in which said chlorides are selected from the group consisting of alkyl dichlorides alkenyl dichlorides and aralkyl dichlorides.

7. A process according to claim 6, in which said dichloride is xylylene dichloride.

8. A process according to claim 6, in which said dichloride is dichlorobutene-2.

9. A process according to claim 1 in which said organic halogen compound (A) is selected from the group consisting of methyl chloride, ethyl chloride, propyl chloride, butyl chloride, amyl chloride, hexyl chloride, heptyl chloride, octyl chloride, nonyl chloride, decyl chloride, dodecyl chloride, tetradecyl chloride, hexadecyl chloride, octadecyl chloride, chlorinated paraffin, cyclohexyl chloride, cyclopentyl chloride dichloroethane, dichloropropane, dichlorobutane, dichloropentane, dichlorohexane, allyl chloride, crotyl chloride, butenyl chloride, propargyl chloride, 1,4-dichlorobutene-2, di(-chloromethyl)ether, di(chloroethyl)ether, di(chloropropyl)ether, di(chlorobutyl)ether, chlorodimethyl ether, chlorodiethyl ether, chlorodipropyl ether, methylchloroethyl ether, propylchloroethyl ether, butylchloroethyl ether, triethylene glycol dichloride, tetraethylene glycol dichloride, polyethylene glycol dichloride, di(chloroethyl)formal, di(chloroethyl)acetal, di(-chloroethyl)butyral, ethylchloroethylacetal, di(chloroethyl)acetone ketal, chloroacetone, dichloroacetone, chlorocyclohexanone, dichlorocyclohexanone, chloroacetone methylketal, dichloroacetone dimethylketal, chloroacetic acid esters, chloroethyl chloroacetate, di(chloroethyl)maleate, di(chloroethyl) succinate, di(-chloroethyl) adipate, di(chloroethyl) phthalate, di(-chloroethyl) carbonate, chlorodimethyl thioether, chlorodiethyl thioether, di(chloromethyl) thioether, di(-chlorethyl) thioeter, chloroacetonitrile, chloropropionitrile, chlorobutyronitrile, chlorocapronitrile, dichloroadiponitrile, benzyl chloride, chlorobenzyl chloride, methylbenzyl chloride, methoxybenzyl chloride, nitrobenzyl chloride, cyanobenzyl chloride, isocyanatomethylbenzyl chloride, xylylene dichloride, chloroxylylene dichloride, methyxylylene dichloride, dimethylxylydine dichloride, methoxyxylylene dichloride, isocyanatomethylxylylene dichloride, trichloropseudocumene, trichloromesitylene, tetrachlorodurene, chloromethylbiphenyl, chloromethylnaphthalene, chloromethylcyclopentadiene, chloromethylfuran, chloromethylpyride, chloromethyldiphenyl ether, di(-chloromethylphenyl) ether, di(chloromethylphenyl)

thioether, di(chloromethylphenyl)sulfone, di(chloromethylphenyl) sulfoxide, dichloromethylbenzidine, phenacyl chloride, chloromethylphenylmethyl ketone, chloromethylphenacyl chloride, chloromethylbenzophenone, di(chloromethyl)benzophenone, chloromethylnaphthylalkyl ethers, di(chloromethylnaphthyl) ether, chloromethylbisphenol A, bis(chlorocyclohexyl), bis(chlorocyclohexyl) ether, bis(chloromethyl)dichlorohexyl, chlorinated petroleum hydrocarbons, chlorinated alkylbenzenes, chloromethylated coal tar hydrocarbons, chloromethylated terpene hydrocarbons, chloromethylated polystyrenes, chloromethylated petroleum resins, chloromethylated coumaroneindene resins, chloromethylated polyterpenes, chloromethylated phenols and chloromethylated phenolic resins and said polyhalogen compound (D) is selected from the group consisting of dichloromethane, dibromomethane, diiodomethane, chloroform, bromoform, iodoform, carbon tetrachloride, carbon tetrabromide, carbon tetraiodide, dichlorodifluoromethane, fluorotrichloromethane, trifluoromethane, trifluorobromomethane, trifluoroiodomethane, trichloroethylene, tetrachloroethylene, perchlorobutadiene, trichloroethane, tetrachloroethane, pentachloroethane, hexachloroethane, tribromoethane, tetrabromoethane, trichloroethylene dibromide, tetrachloroethylene dibromide, tetrafluoroethylene dichloride, trifluorotrichloroethane, tetrafluoroethylene dibromide, trifluorochlorodibromethane, hexafluoropropene dichloride, hexafluoropropene dibromide, fureons, perfluorobutadiene tetrachloride, perfluorobutadiene tetrabromide, chloral, chloral acetal, pentachloroacetone, pentachloroacetone ketal, hexachloroacetone, pentachloroacetone, pentachloroacetone ketal, hexachloroacetone, hexachloroacetone ketal, pentafluoroacetone, pentafluoroacetone ketal, hexafluoroacetone, hexafluoroacetone ketal, trichlorotrifluoroacetone, tetrachlorodifluoroacetone, pentachlorofluoroacetone, dichlorotetrafluoroacetone, chloropentafluoroacetone, trichloroacetonitrile, trifluoroacetonitrile, tribromoacetonitrile, dichloroacetonitrile, dichlorofluoroacetonitrile, chlorodifluoroacetonitrile, trifluoroacetic acid esters, perfluorofatty acid esters, perfluoroalkanes, perfluoroalkenes, perfluoroalkyl ethers, perfluoroalkylbenzens, perfluorofatty acid amides, benzal chloride, chlorobenzal chloride, benzotrichloride, chlorobenzotrichloride, benzal bluoride, chlorobenzal fluoride, benzotrifluroide, chlorobenzotrifluoride, trifluoromethylbenzal fluoride, trifluoromethylbenzotrifluoride, chlorodifluoromethylbenzene, dichlorofluoromethylbenzene, bromodifluoromethylbenzene, dibromofluoromethylbenzene, chlorodifluoromethylbenzotrifluoride, dichlorofluoromethylbenzotrichloride, dichlorofluoromethylbenzotrifluoride, perfluoroalkyl thioethers, perfluoroalkyl amines, perfluoroalkyl phosphoric acid esters, perfluroalkyl chlorides, perfluroalkyl bromides, and perfluoroalkyl iodides.

10. A process according to claim 9 in which said polyhalogen compound (D) is added in advance of the reaction to the organic halogen compound (A) or to the solvent (C).

* * * * *

UNITED STATES PATENT AND TRADEMARK OFFICE
CERTIFICATE OF CORRECTION

PATENT NO. : 4 059 610

DATED : November 22, 1977

INVENTOR(S) : Susumu Handa, Yoshiaki Tanaka, Atsushi Nishibata, Sadashi Ueda, Yoshiaki Inamoto, Masahiro Saito, Fumio Tanimoto and Hisao Kitano It is certified that error appears in the above-identified patent and that said Letters Patent are hereby corrected as shown below:

Column 13, line 44; change "amines" to ---amides---.

Signed and Sealed this

Fourteenth Day of March 1978

[SEAL]

Attest:

RUTH C. MASON
Attesting Officer

LUTRELLE F. PARKER
Acting Commissioner of Patents and Trademarks